United States Patent [19]

Brugger et al.

[11] Patent Number: 5,693,008
[45] Date of Patent: Dec. 2, 1997

US005693008A

[54] DIALYSIS BLOOD TUBING SET

[75] Inventors: James M. Brugger, Boulder; Keith J. Manica; William G. Palsulich, both of Lakewood, all of Colo.

[73] Assignee: COBE Laboratories, Inc., Lakewood, Colo.

[21] Appl. No.: 480,856

[22] Filed: Jun. 7, 1995

[51] Int. Cl.$^6$ ................................................. A61M 37/00
[52] U.S. Cl. ............................. 604/4; 604/86; 128/672
[58] Field of Search ........................... 604/30, 83, 86, 604/118, 122, 125, 128, 141, 4, 5, 6, 64, 65, 280, 283, 905; 73/715, 716; 128/668, 672

[56] References Cited

U.S. PATENT DOCUMENTS

| | | | |
|---|---|---|---|
| 3,713,341 | 1/1973 | Madsen et al. | 73/406 |
| 3,908,653 | 9/1975 | Kettering | 604/5 |
| 4,303,068 | 12/1981 | Zelman | 604/5 |
| 4,666,598 | 5/1987 | Heath et al. . | |
| 4,758,228 | 7/1988 | Williams | 604/118 |
| 4,798,580 | 1/1989 | DeMeo et al. | 604/30 |
| 4,819,653 | 4/1989 | Marks . | |
| 5,041,215 | 8/1991 | Chamberlain, Jr. et al. . | |
| 5,116,308 | 5/1992 | Hagiwara | 604/5 |
| 5,203,340 | 4/1993 | Gustafson et al. | 128/675 |
| 5,242,406 | 9/1993 | Gross et al. | 604/141 |
| 5,322,516 | 6/1994 | Brugger . | |
| 5,346,477 | 9/1994 | Edwards et al. | 604/141 |
| 5,348,539 | 9/1994 | Herskowitz | 604/141 |
| 5,394,732 | 3/1995 | Johnson et al. . | |
| 5,399,166 | 3/1995 | Laing | 604/141 |

FOREIGN PATENT DOCUMENTS

| | | |
|---|---|---|
| 0 142 866 | 5/1985 | European Pat. Off. . |
| 0 341 488 | 11/1989 | European Pat. Off. . |
| 2176595 | 12/1986 | United Kingdom . |
| 90/12606 | 11/1990 | WIPO . |

OTHER PUBLICATIONS

The Extracorporeal Circuit, by Hans–Dietrich Polaschegg, Seminars in Dialysis, Sep.–Oct., 1995, vol. 8, No. 5, pp. 299–304.

Slow Nocturnal Home Hemodialysis, by Dr. Pierratos, Michaelene Ouwendyk, Robert Francoeur, Lynda Wallace, William Sit, Dr. Stephen Vas, and Dr. Robert Udall, Dialysis and Transplantation Oct., 1995, vol. 24, No. 10, pp. 557, 558 and 576.

Primary Examiner—John G. Weiss
Assistant Examiner—Ki Yong O
Attorney, Agent, or Firm—Bruce R. Winsor; Edna O'Connor

[57] ABSTRACT

A combination pressure pod and access site apparatus is suitable for use in a medical tubing set. The combination pressure pod and access site comprises a pressure sensing chamber and a measured fluid chamber separated by a pressure transmissive diaphragm. An access site having a needle or needle-less septum is in fluid communication with the measured fluid chamber and permits and withdrawing fluids from, the measured fluid chamber through the access site. One or more of the combination pressure sites and access sites may be provided in a simplified blood tubing set for an extracorporeal blood treatment apparatus, such as a hemodialysis apparatus.

20 Claims, 4 Drawing Sheets

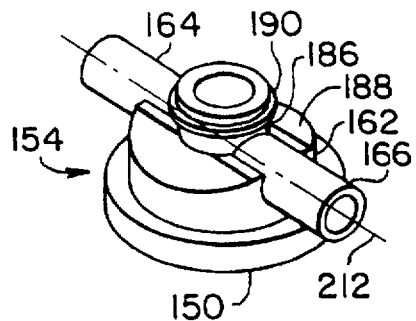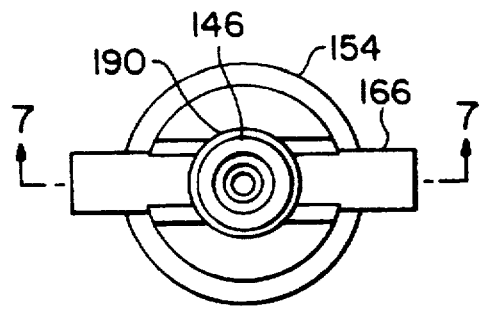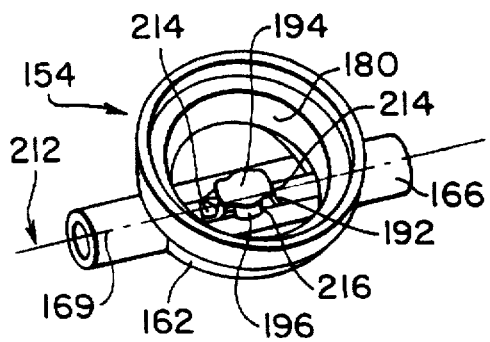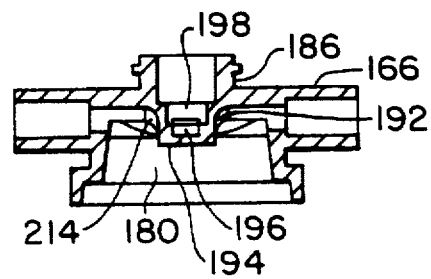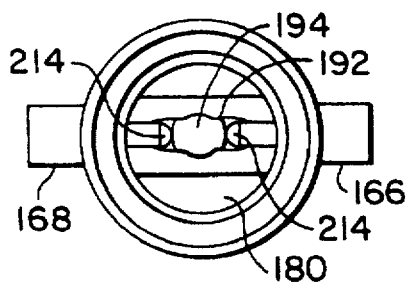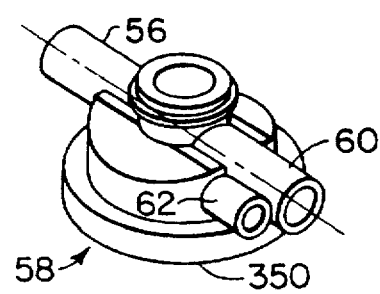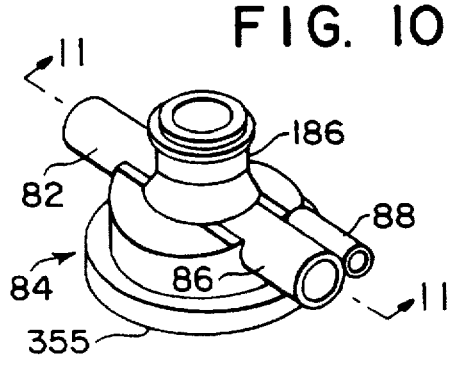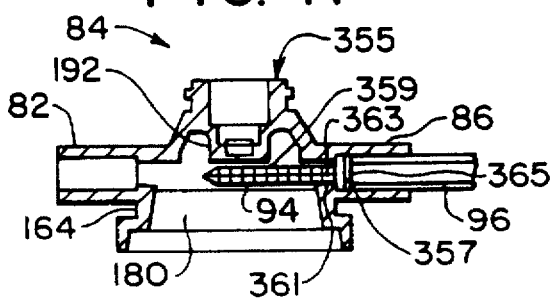

DIALYSIS BLOOD TUBING SET

FIELD OF THE INVENTION

The present invention relates to blood tubing sets for use in dialysis procedures.

BACKGROUND OF THE INVENTION

Tremendous advances have been made in the treatment of end stage renal disease. Through dialysis with artificial kidneys it is possible to keep patients alive, and to permit them to lead relatively normal lives, even after loss of kidney function. One form of dialysis is hemodialysis, where the patient's blood is removed from the patient's body, anticoagulated, circulated by an extracorporeal tubing circuit through an artificial kidney, or dialyzer, to remove toxic substances, such as urea and creatinine, as well as excess fluid, and returned to the patient. Hemodialysis is typically performed on a patient about every three days.

The extracorporeal tubing circuit typically consists of cannulae for drawing blood from and returning blood to a patient, the dialyzer and a blood tubing set. The blood tubing set typically comprises a plurality of sections of medical tubing, bubble traps or drip chambers (collectively "bubble traps" herein), pressure monitoring sites, air bubble detection sites, access sites connectors, clamps, peristaltic pump headers and accessories of various sorts. Pressure monitoring sites are typically disposable pressure pods which transmit the pressure of blood, or another fluid, to a pressure sensor while simultaneously isolating the blood or other fluid from the pressure sensor. Access sites are typically disposable septa and associated housing for sampling the patient's blood or adding medication. Access sites may require two hands to operate, one to hold the site steady, another to operate a sampling or injection syringe. This may increase the risk of needle sticks to the hand holding the access site.

Because hemodialysis must be performed frequently, it is important to keep the cost of each treatment as low as possible. Further, it is desirable to minimize the amount of blood outside a patient's body in the extracorporeal circuit, thereby minimizing the stress on the patient as well as minimizing the potential for trauma to the blood. Bubble traps typically retain a relatively large volume of blood during normal operation. Blood trauma also can occur at an air-blood interface such as are found in typical bubble traps and drip chambers. It would further be advantageous to eliminate or reduce the need to add anticoagulant to the blood, further reducing the physical stress on the patient.

It is against this background that the blood tubing set of the present invention developed.

SUMMARY OF THE INVENTION

One significant aspect of the present invention is a combined pressure sensing pod and needle access site ("pod/site" herein) which reduces treatment cost by reducing the cost of the blood tubing set. The pod/site combines, in a single device, the functions of transmitting pressure from blood or other fluid to a pressure sensor without the blood contacting the pressure sensor and providing a site for injecting fluids into or withdrawing fluids from the blood or other fluid. The cost of the blood tubing set is reduced in accordance with this aspect of the invention by reducing the manufacturing cost of the pressure pods and needle access sites by combining them in a single part and further by reducing tubing set assembly cost by reducing the number of parts. In accordance with this aspect of the invention, a needle access site is provided on a front or top face of a pressure pod, thus combining two functions into a single device and achieving the additional result that the needle access site may be used to remove air from the pod/site. Further in accordance with this aspect of the invention, a needle guard and flow diverter is provided to protect the diaphragm of the pressure pod from accidental needle punctures and to prevent blood flowing in the pod/site from flowing directly through the pod/site. The flow diverter forces the pod/site to trap air, which may subsequently be removed with a needle through the access site. Further, the pod/site is typically held securely, obviating the need to hold the pod/site during sampling from or injecting into the pod/site.

Another significant aspect of the present invention is a simplified blood tubing set incorporating the pod/sites to achieve still further significant benefits. In accordance with this aspect of the invention a blood tubing set is provided which facilitates the detection of, and protection of the patient against, the well known problems of air bubbles, without the use of the typical bubble traps. In accordance with this aspect of the invention, a pod/site is provided at a location in the blood tubing set normally occupied by an arterial bubble trap. This arterial pod/site is further provided with a saline line connection to permit the addition of saline solution to the blood tubing set, as for priming. Further in accordance with this aspect of the invention a pod/site is provided at a location typically occupied by a venous bubble trap. This venous pod/site is provided with a filter to prevent particulate matter from entering a patient and with a connection to permit adding medication to the blood returning to the patient.

Cost is reduced by eliminating the two bubble traps and by reducing assembly cost by reducing the number of parts in the blood tubing set. Further, the extracorporeal blood volume is greatly reduced by eliminating the bubble traps, thereby reducing blood trauma potential. Blood trauma potential is further reduced by the elimination of the air-blood interfaces of the bubble traps. The reduction in extracorporeal blood volume, and therefore the amount of time that blood is circulated outside the patient's body, may reduce or eliminate the need for anticoagulant.

Further significant aspects of the present invention will be apparent to one skilled in the art from the drawings, detailed description of the preferred embodiment and the claims.

BRIEF DESCRIPTION OF THE DRAWINGS

FIG. 4 is a top perspective view of a portion of the pod/site shown in FIG. 3.

FIG. 5 is a bottom perspective view of a portion of the pod/site shown in FIG. 4.

FIG. 6 is a plan view of the portion of the pod/site shown in FIG. 4.

FIG. 7 is a sectional side view of the portion of the pod/site shown in FIG. 6 viewed from line 7—7.

FIG. 8 is a bottom view of the portion of the pod/site shown in FIG. 4.

FIG. 9 is a top perspective of an alternative embodiment of the portion of the pod/site shown in FIG. 4.

FIG. 10 is a top perspective view of a further alternative embodiment of the pod/site shown in FIG. 4.

FIG. 11 is a side sectional view of the portion of the pod/site shown in FIG. 10, viewed from line 11—11.

DETAILED DESCRIPTION OF THE PREFERRED EMBODIMENT

Figure 1:
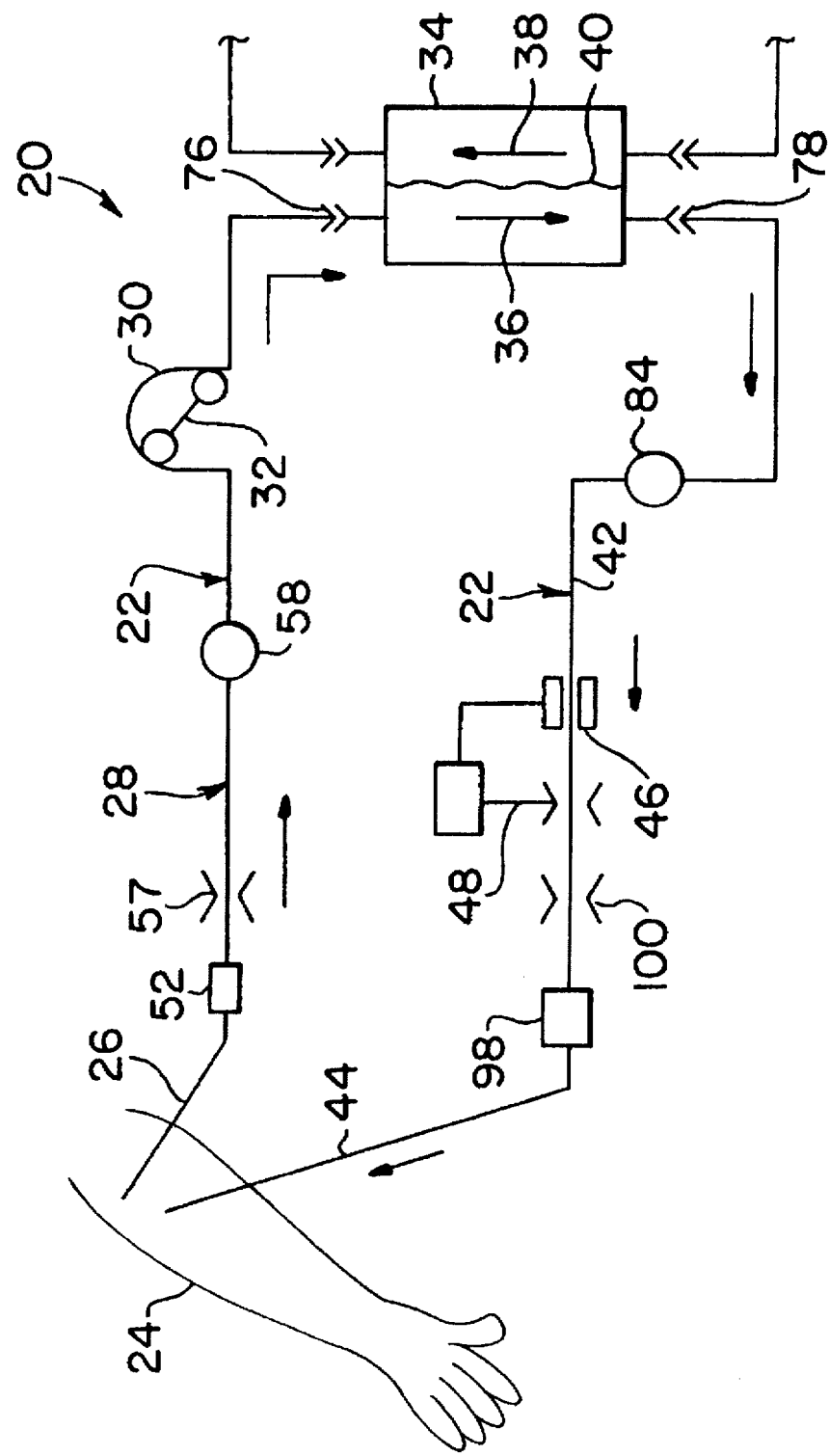
FIG. 1 is a schematic diagram of a hemodialysis apparatus having a blood tubing set in accordance with the present invention.

FIG. 1 illustrates a hemodialysis apparatus 20 incorporating the blood tubing set 22 of the present invention. Blood, typically referred to as arterial blood, is withdrawn from a patient 24 through an arterial cannula and cannula line 26 into an arterial segment 28 of the blood tubing set 22. The arterial segment 28 includes a pump header tubing section 30 which is acted on by a rotor of a peristaltic pump 32 to move the blood through the hemodialysis apparatus 20. The blood then passes into a dialyzer 34 which is divided into a blood chamber 36 and a dialysate chamber 38 by a semi-permeable membrane 40. Substances such as urea and creatanine, as well as excess fluid, are transferred from the blood in the blood chamber 36 across the semi-permeable membrane 40, to dialysate flowing in the dialysate chamber 38 in a well known manner. The dialysate chamber 38 of the dialyzer 34 is connected to a source of fresh dialysate (not shown) and a disposal line for spent dialysate (not shown). Blood exits the blood chamber 36 of the dialyzer 34 into a venous segment 42 of the blood tubing set 22 and from there returns to the patient 24 through a venous cannula and cannula line 44.

The hemodialysis apparatus 20 is provided with a bubble detector 46 of a type which can detect the presence of bubbles in the fluid flowing in the tubing through the walls of the tubing of the tubing set 22. Such a bubble detector is disclosed in U.S. Pat. No. 5,394,732 to Johnson et al., which is assigned to the assignee of the present invention, the entire disclosure of which is incorporated herein by reference. The bubble detector 46 may provide a signal to an automatic venous clamp 48 to cause the automatic venous clamp 48 to close, interrupting the flow of blood to the patient 24 in the event the bubble detector 46 detects air bubbles which are potentially harmful to the patient 24.

Figure 2:
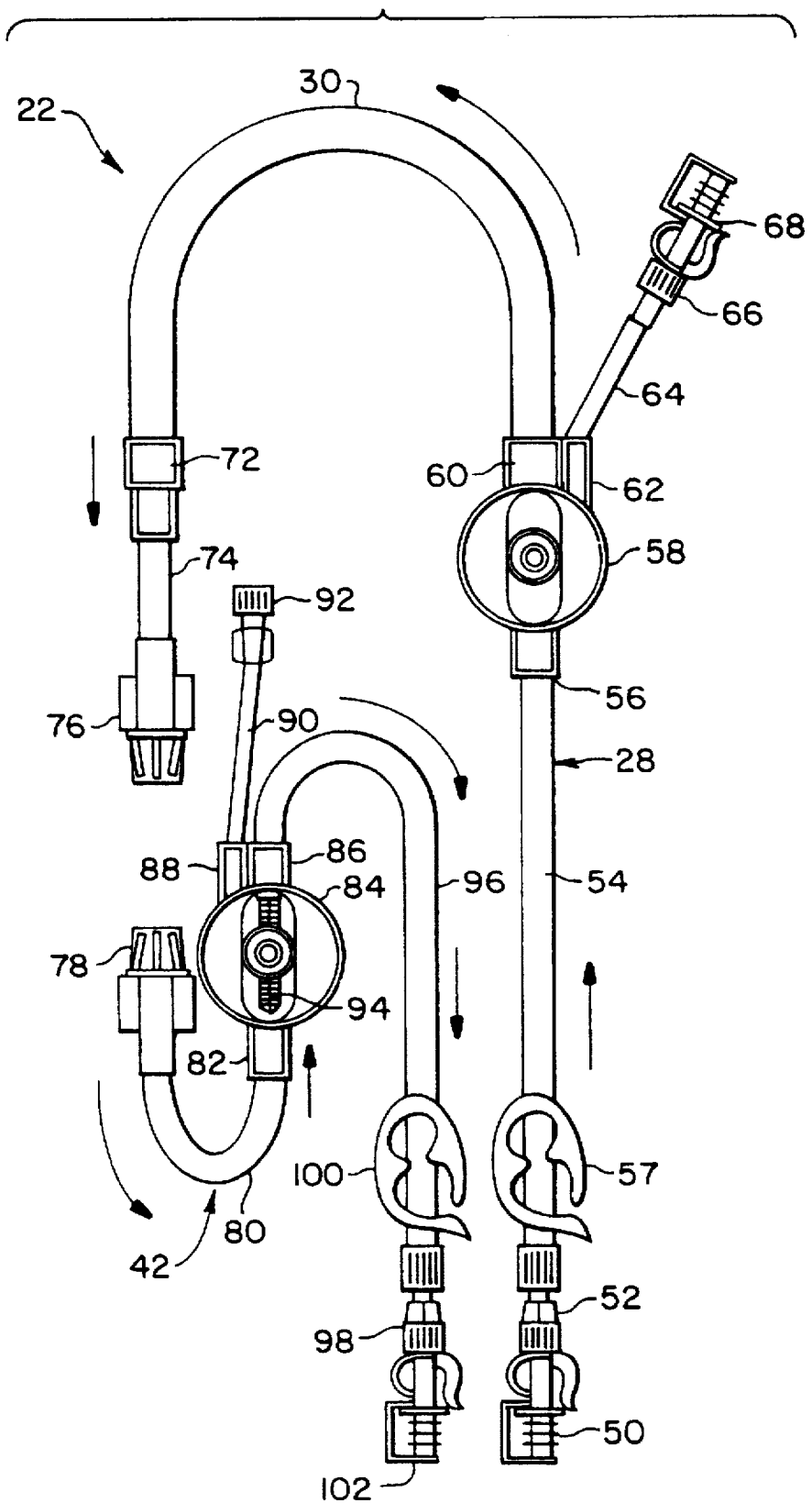
FIG. 2 is a pictorial representation of the blood tubing set of FIG. 1.

The blood tubing set 22 will be described in more detail by reference to FIG. 2. The arterial segment 28 will be described sequentially from the point where the arterial cannula and cannula line 26 connects to the arterial segment 28 of blood tubing set 22, to the point where the arterial segment 28 connects to the dialyzer 34. The venous segment 42 will then be described sequentially from the point where the venous segment 42 connects to the dialyzer 34, to the point where the venous segment 42 connects to the venous cannula and cannula line 44.

The arterial segment 28 of the blood tubing set 22 is a continuous flow communication path comprising an arterial capped connector 50, adapted to be connected to a priming waste handling system, such as that described in U.S. Pat. No. 5,041,215 to Chamberlain et al., which is assigned to the assignee of the present invention, the entire disclosure of which is incorporated herein by reference. The arterial capped priming connector 50 is then connected to an arterial rotating collar luer connector 52 which connects to the arterial cannula and cannula line 26. A first tubing section 54 connects the arterial rotating collar luer connector 52 to an inlet 56 of an arterial pod/site 58. A manually activated arterial pinch clamp 57 is interposed on the first tubing section 54 at a location near the arterial rotating collar luer connector 52.

The arterial pod/site 58 has a principal outlet 60 and a secondary outlet 62. A second tubing section 64 connects the secondary outlet 62 of the arterial pod/site 58 to a luer lock connector 66 which is, in turn, connected to a saline capped priming connector 68. The saline capped priming connector 68 is similar to the arterial capped priming connector 50 and facilitates introduction of saline solution and other fluids into the tubing set.

The pump header tubing section 30, which has a diameter and length coordinated to interfit with the peristaltic pump 32 (FIG. 1), extends from the principal outlet 60 of the arterial pod/site 58 to a ferrule 72, which may be a reducing ferrule.

A third tubing segment 74 then extends from the ferrule 72 to an arterial dialyzer connector 76, which is adapted to connect the arterial segment 28 of the tubing set 22 to the dialyzer 34. The arterial dialyzer connector 76 may be a luer-lock connector or the like.

The venous segment 42 of the blood tubing set 22 comprises a venous dialyzer connector 78, which may also be a luer-lock connector or the like which is connected by a fourth section of tubing 80 to an inlet 82 of a venous pod/site 84. The venous pod/site 84 has a principal outlet 86 and a secondary outlet 88. The secondary outlet 88 of the venous pod/site 84 is connected by a fifth tubing section 90 to a luer connector 92 which is adapted to receive dispensing apparatus, such as a luer connected syringe (not shown), for medication to be administered to the patient 24 (FIG. 1) by injection in the patient's blood flowing in the venous segment 42.

The venous pod/site has within it a tubular particulate filter 94, which prevents particulates entering the venous pod/site 84 through the inlet 82 from exiting the pod/site 84 through the principal outlet 86. The principal outlet 86 of the venous pod/site 84 is connected by a sixth tubing section 96 to a venous rotating collar luer connector 98. Interposed on the sixth tubing segment 96 near the venous rotating collar luer connector 98 is a manually activated venous pinch clamp 100. The sixth tubing section 96 interfits with the air bubble detector 46 and automatic venous clamp 48 between the venous pod/site 84 and the venous pinch clamp 100. The rotating collar luer connector 98 is then terminated with a venous capped priming connector 102.

The tubing set 22 of the present invention is assembled using conventional medical tubing connectors and connection techniques well known in the art.

The general construction and function of pressure pods is described in U.S. Pat. No. 4,666,598 which is assigned to the assignee of the present invention, the entire disclosure of which is incorporated herein by reference. Access sites take many forms. Exemplary access sites are described in U.S. patent application Ser. No. 08/483,740, Internally Lubricated Elastomers for Use in Biomedical Applications filed Jun. 7, 1995, assigned to the assignee of the present invention which is a continuation-in-part of U.S. patent application Ser. No. 08/047,856, filed Apr. 15, 1993, the entire disclosure of which is incorporated herein by reference. Further examplary access sites are described in U.S. Pat. No. 5,322,516 which is assigned to the assignee of the present invention and which is incorporated herein by reference in its entirety.

Figure 3:
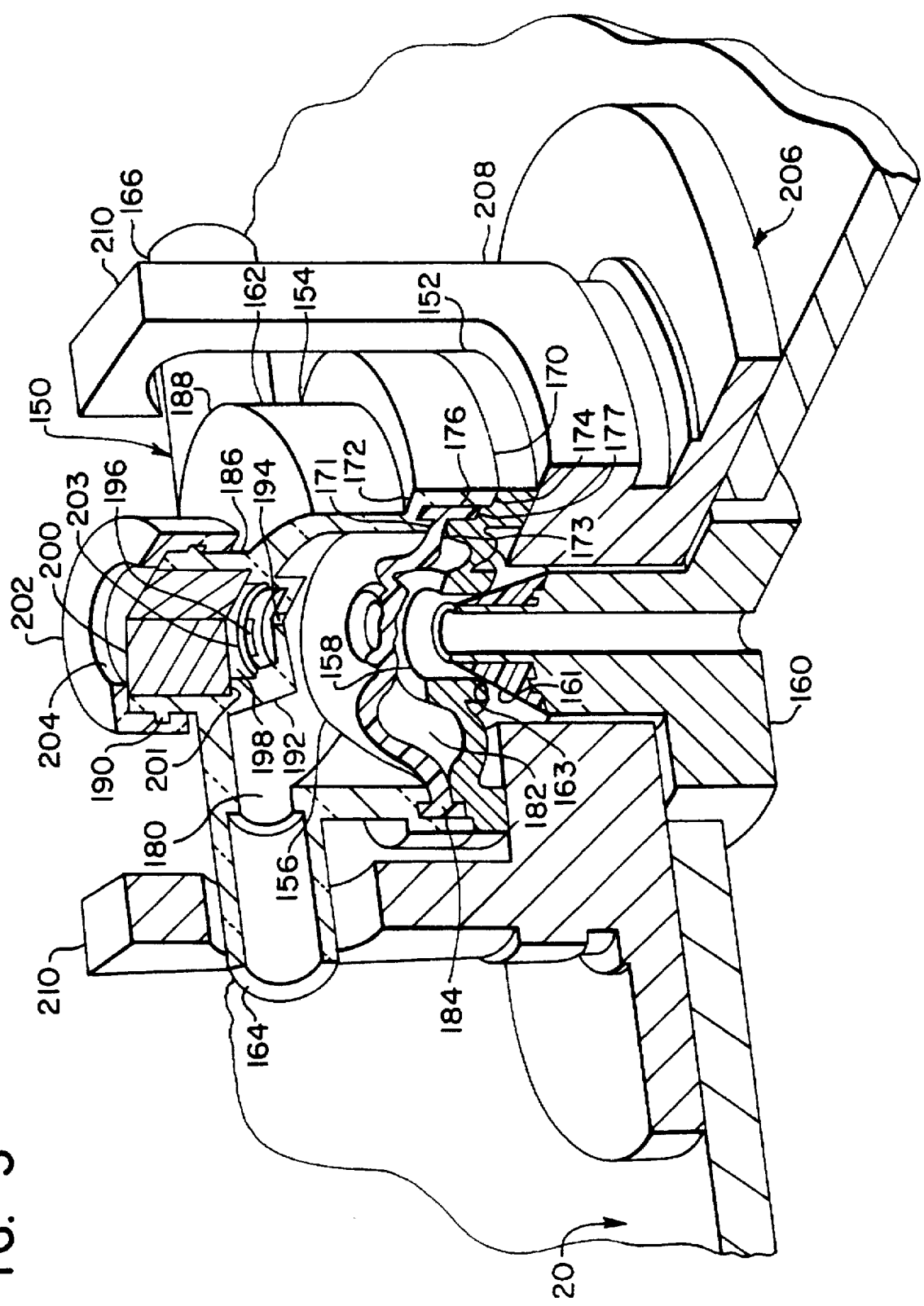
FIG. 3 is a partially cut away perspective view of a pod/site of the present invention mounted to a pod/site holder.

The combination pressure pod/access site 150 will be described by reference to FIG. 3. It will be appreciated by one skilled in the art that this description covers one specific pressure pod design and one specific access site design but the invention is not so limited. In particular, it is within the scope of the present invention to combine many different pressure pod designs with many different access site designs in order to achieve the objects of the present invention.

The pod/site 150 of the present invention comprises a pod base 152, a pod cap 154 and an elastomeric pressure transmission diaphragm such as a silicone diaphragm 156, sandwiched sealingly between the pod cap 154 and the pod base 152. The pod base 152 and pod cap 154 may be injection molded from any of a variety of plastic materials, such as polyethylene terephthalate glycol (PETG), selected at least in part for their biocompatible properties. The pod cap 154 is preferably transparent.

The pod base 152 further comprises a generally circular disk-like member with a central orifice 158 that mates removably and sealingly with a pressure sensing member 160. A resilient elastomeric frustoconical seal 161 surrounds the pressure sensing member 160 and seals the orifice 158 to the pressure sensing member 160 at a lower radiused edge 163 of the orifice 158. The pod cap 154 comprises a generally cylindrical chamber 162 having two co-linearly extending tubing connections 164, 166 in fluid communication with the interior 180 of chamber 162. The pod cap 154 has a bottom portion 170 having a generally annularly extending peripheral L-shaped flange 172 which matches a annularly extending upwardly facing peripheral mating ledge 174 on the pod base 152. A downward facing, annularly extending cap ridge 171 is located in the interior 180 of the pod cap 154 inwardly of the flange 172. An upward facing annularly extending base ridge 173 matching the cap ridge 171 is located on the pod base 152. The pod base 152 interfits with the bottom 170 of the pod cap 154 with the flange 172 of the pod cap 154 mating with the mating ledge 174 of the base 152. The flange 172 and cap ridge 171 of the cap 154 and the base ridge 173 and an annular ledge 177 inward of the mating ledge 174 of the base 152 cooperate to define an annular retention cavity 176 opening into an interior 180 of the chamber 162 of the cap 154.

The interior 180 of the chamber 162 receives and retains a portion of the fluid, typically blood, the pressure of which is to be measured by the pod/site 150. The diaphragm 156 is generally disc-like and may have a shape adapted to facilitate the transfer of pressures from the fluid in the interior 180 of the chamber 162 to a pressure measuring space 182 between the pod base 152 of the pod/site 150 and the diaphragm 156, and from there to the pressure sensing element 160. The diaphragm has a thickened peripheral portion 184 which is retained in the retention cavity 176. The remainder of the disk-like diaphragm 156 cooperates with the cap ridge 171 and the base ridge 173 to form a fluidly sealed resilient pressure transmissive barrier between the interior 180 of the chamber 162 of the pod cap 154 and the pressure metering space 182 between the diaphragm 156 and the pod base 152. The pod base 152 and pod cap 154 are typically joined by ultrasonic welding.

The cap further comprises an access extension 186, also in fluid communication with the interior 180. The access extension 186 is a generally tubular member extending from the top 188 of the cap 154. It should be understood that the terms top and bottom are used for reference only. The pod/site may be installed in several orientations, a common one being with the cap top 188 facing away from a dialysis machine 20 and the bottom 150 of the cap 154 towards the machine. The access extension 186 has an exterior peripheral ring 190. Extending downwardly from the access extension 186, and in fluid communication with the interior 180 of the chamber 162 is a needle guard portion 192. The needle guard portion has a solid floor 194. The needle guard portion 192 further has a wall that has lateral windows 196 which are positioned so that fluid entering or leaving the access site 150 through the tubing connections, 164, 166 cannot flow directly into the windows 196 of the needle guard portion 192, but rather are diverted by the needle guard portion's 192 extension into the interior 180 of the chamber 162 to flow around the needle guard portion, 92 when flowing from one inlet tube 164 to the other tube 166 or the reverse.

Fluid may only flow into and out of the interior 180 of the chamber from and to an interior 198 of the needle guard portion 192 through the windows 196. The windows 196 are preferably too small for the smallest expected needles to pass through the windows, preferably no more than 0.020 inches in at least one dimension, but large enough to pass air and blood freely.

A septum plug 200 is inserted into the access extension 186 into the interior 198 of the access extension 186. A shoulder 201 defines an orifice 203 in the interior 198 of the access extension 186 that is smaller than the diameter of the septum plug 200. The shoulder 201 in the interior 198 of the access extension 186 retains and sealingly mates with the septum plug 200. The septum plug 200 is held in place by a retention ring 202 which fits over the access extension 186 and mates with the peripheral ring 190 of the access extension 186 and has a lip 204 for retaining the septum plug 200 in place in the access extension 186. The septum plug may be an injection molded cylinder of a silicone impregnated thermoplastic styrene-ethylene/bytylene-styrene block polymer having a Shore A durometer hardness of 15 to 40, such as C-FLEX™ manufactured by Consolidated Polymer Technologies, Inc.

The septum may be any of several types including a septum for a sharp needle, a septum for a blunt needle, or a pre-split septum for a blunt needle or cannula.

The needle guard portion 192 is located so that the floor 194 of the needle guard portion is above the diaphragm 156 and so that a sharp or blunt needle or cannula (not shown) penetrating the septum plug 200 will be blocked by the floor 194 and cannot damage the diaphragm 156.

The pod site may be releasably mounted to a hemodialysis apparatus 20 by a pod/site mounting assembly 206 which comprises the pressure sensor 160 and a pod/site retention member 208 which may, for example, retain the pod/access site by a pair of clip arms 210 which interfit with, and hook around, the tubing connections 164, 166. The resilient frustoconical seal 161 of the pressure sensor 160 is compressed when the pod/site 150 is installed, biasing the pod/site upward to retain it in the clip arms 210 of the pod/site retention member 208.

The cap will be described in more detail with reference to FIGS. 4–8. The cap comprises the chamber 162 and the two tubing connections 164, 166 which extend along, and define a flow path about, an axis 212 and which are in fluid communication with the interior 180 of the chamber 162. The access extension 186 with its ring 190 extends vertically from the cap. The needle guard portion 192 extends into the flow path defined by the axis 212 from the access site extension 186. The needle guard portion 192 partially obstructs the flow path along the axis 212 so that fluid entering either tubing connection 164, 166 is prevented from flowing in a straight path through the interior 180 of the cap 154 to the other tubing connection 164, 166 but is instead diverted to one side or the other, or below the floor 194, of the needle guard portion 192. The needle guard portion 192 floor 194 is connected to the top 188 of the chamber 162 by a vertically extending wall 214. The vertically extending walls 214 generally block the direct passage of fluid between the tubing connections 164, 166 and are contoured to smoothly direct impinging flow downward. Interposed in the wall 214, on an axis 216 perpendicular to the axis 212 of the tubing connectors 164, 166, are the two windows 196 which provide fluid communication between the interior 180 of the cap 154 and the interior 198 of the access extension 186. The tubing connections 56, 62, 82, 86, 88, 164, 166 may be the typical welded push fit sockets for typical medical flexible tubing as are well known in the art. The tubing connections 56, 62, 82, 86, 88, 164, 166 may be the typical welded push fit sockets for typical medical flexible tubing as are well known in the art.

FIG. 9 illustrates a cap 350 adapted for use on the simplified blood tubing set 22 of the present invention for use as the arterial pod/site 58. The arterial cap 350 comprises, in addition to the co-linear tubing connections 56, 60, a secondary tubing connection of smaller diameter 62 offset from and parallel to, the axis 212 defined by the co-linear tubing connectors 60, 56. This offset secondary tubing connector 62 adjacent to one of the co-linear tubing connections 60 and is further in fluid communication with the interior 180 of the cap 350.

FIGS. 10 and 11 illustrate another embodiment of the cap 355 which may be adaptable for use on the venous pod/site 84. In this embodiment the venous cap 355 comprises the secondary tubing connection 88 offset from the axis of the co-linear tubing connectors 82,86 and adjacent to, and parallel to one of the co-linear connectors 86.

The tubular filter 94 is installed within the venous cap 355. The tubular filter 94 has a flange 357 at its base and a porous tubular filtration portion 359. A shoulder in one of the tubing connectors 86 has a shoulder 361 that defines an orifice 363 into the interior 180 of the chamber 164 that is smaller than the flange 357 and larger than the diameter of the filter portion 359. The filter 94 is installed by passing the filter portion 359 through the orifice until the flange 357 is sealingly engaged with the shoulder 361. The filter 94 is then retained by the end 365 of a medical tubing section 96 secured in the tubing connector 86 against the flange 361, as has been well known for many years.

To accommodate the filter 92 the access extension 186 may be of a length as necessary to bring the needle guard portion 192 above the filter 92.

A presently preferred embodiment of the present invention has been described. Many variations of the invention may be made which are within the spirit and scope of the invention as claimed in the following claims.

The invention claimed is:

1. A combination pressure pod and access site apparatus for use in a medical tubing set comprising:
   a pressure sensing chamber having a pressure measuring space;
   a measured fluid chamber for receiving fluid;
   a pressure transmissive diaphragm sealingly separating the pressure measuring space from the measured fluid chamber wherein the diaphragm prevents received fluid from flowing into the pressure measuring space;
   an access site in fluid communication with the measured fluid chamber; and
   a septum forming a portion of the access site that permits injecting fluids into, and withdrawing fluids from, the measured fluid chamber through the access site.

2. An apparatus as defined in claim 1 further comprising:
   a needle guard configured and located to prevent damaging the pressure transmissive diaphragm during use of the septum while permitting fluid to be transferred from the measured fluid chamber to the access site and from the access site to the measured chamber.

3. An apparatus as defined in claim 1 further comprising at least one tubing connection in fluid communication with the measured fluid chamber.

4. An apparatus as defined in claim 3 wherein the at least one tubing connection comprises:
   two co-linear tubing connections each in fluid communication with the measured fluid chamber; further comprising:
   a flow diverter to prevent flow entering the measured fluid chamber from flowing in a straight line from one of the tubing connections to another one of the tubing connections.

5. An apparatus as defined in claim 4 further comprising a third tubing connection in fluid communication with the measured fluid chamber.

6. An apparatus as defined in claim 4 further comprising:
   a needle guard configured and located to prevent damaging the pressure transmissive diaphragm during use of the septum while permitting fluid to be transferred from the measured fluid chamber to the access site and from the access site to the measured chamber.

7. An apparatus as defined in claim 3 further comprising a filter mutually fitting with the tubing connection.

8. Blood tubing set apparatus for use with an extracorporeal blood treatment apparatus comprising:
   at least one combination pressure pod and access site for use in a medical tubing set comprising:
   a pressure sensing chamber having a pressure measuring space;
   a measured fluid chamber for receiving fluid;
   a pressure transmissive diaphragm sealingly separating the pressure measuring space from the measured fluid chamber wherein the diaphragm prevents received fluid from flowing into the pressure measuring space;
   an access site in fluid communication with the measured fluid chamber; and
   a septum forming a portion of the access site that permits injecting fluids into, and withdrawing fluids from, the measured fluid chamber through the access site.

9. A blood tubing set apparatus as defined in claim 8 wherein:
   the at least one combination pressure pod and access site further comprises:
   a needle guard configured and located to prevent damaging the pressure transmissive diaphragm during use of the septum while permitting fluid to be transferred from the measured fluid chamber to the access site and from the access site to the measured fluid chamber.

10. A blood tubing set apparatus as defined in claim 9 wherein:
    the at least one combination pressure pod and access site comprises:
    two co-linear tubing connections each in fluid communication with the measured fluid chamber;
    a flow diverter to prevent flow entering the measured fluid chamber from flowing in a straight line from one of the tubing connections to another one of the tubing connections; and
    a third tubing connection in fluid communication with the measured fluid chamber.

11. A blood tubing set apparatus as defined in claim 9 wherein:

the at least one combination pressure pod and access site comprises:
two co-linear tubing connections each in fluid communication with the measured fluid chamber;
a third tubing connection in fluid communication with the measured fluid chamber; and
a filter mutually fitting with one of the co-linear tubing connections.

12. A blood tubing set apparatus for use with an extracorporeal blood treatment apparatus comprising:

a first tubing segment having a first combination pressure pod and access site interposed therein, said first combination pressure pod and access site comprising:
a first pressure sensing chamber having a first pressure measuring space;
a first measured fluid chamber for receiving fluid;
a first pressure transmissive diaphragm sealingly separating the first pressure measuring space from the first measured fluid chamber wherein the first diaphragm prevents received fluid from flowing into the first pressure measuring space;
a first access site in fluid communication with the first measured fluid chamber; and
a first septum forming a portion of the first access site that permits injecting fluids into, and withdrawing fluids from, the first measured fluid chamber through the first access site; and a second tubing segment having a second combination pressure pod and access site interposed therein, said second combination pressure pod and access site comprising:
a second pressure sensing chamber having a second pressure measuring space;
a second measured fluid chamber for receiving fluid;
a second pressure transmissive diaphragm sealingly separating the second pressure measuring space from the second measured fluid chamber wherein the second diaphragm prevents received fluid from flowing into the second pressure measuring space;
a second access site in fluid communication with the second measured fluid chamber; and
a second septum forming a portion of the second access site that permits injecting fluids into, and withdrawing fluids from, the second measured fluid chamber through the second access site.

13. A blood tubing set apparatus as definedin claim 12 wherein:

at least one of the first and the second combination pressure pod and access sites further comprises:
a needle guard configured and located to prevent damaging the corresponding pressure transmissive diaphragm during use of the corresponding septum while permitting fluid to be transferred from the corresponding measured fluid chamber to the corresponding access site and from the corresponding access site to the corresponding measured fluid chamber.

14. A blood tubing set apparatus as defined in claim 12 wherein:

the first combination pressure pod and access site comprises:
two co-linear tubing connections each in fluid communication with the measured fluid chamber and connected interposingly to the first tubing segment;
a flow diverter to prevent flow entering the measured fluid chamber from flowing in a straight line from one of the tubing connections to another one of the tubing connections; and
a third tubing connection in fluid communication with the measured fluid chamber.

15. A blood tubing set apparatus as defined in claim 12 wherein:

the second combination pressure pod and access site comprises:
two co-linear tubing connections each in fluid communication with the measured fluid chamber and connected interposingly to the second tubing segment;
a third tubing connection in fluid communication with the measured fluid chamber; and
a filter mutually fitting with one of the co-linear tubing connections.

16. A blood tubing set apparatus as defined in claim 12 wherein:

the extracorporeal blood treatment apparatus comprises a dialysis apparatus;
the first tubing segment is a dialysis arterial tubing segment; and
the second tubing segment is a dialysis venous tubing segment.

17. The apparatus of claim 2 wherein the needle guard further comprises:

a needle guard portion extending into the measured fluid chamber and a floor on the needle guard portion wherein a needle or cannuala inserted into the access site is blocked by the floor from damaging said pressure transmissive diaphragm.

18. The apparatus of claim 17 wherein the needle guard portion further comprises:

a wall and at least one window in the wall for allowing received fluid to flow into and out of the needle guard portion.

19. The apparatus of claim 8 wherein the needle guard further comprises:

a needle guard portion extending into the measured fluid chamber and a floor on the needle guard portion wherein a needle or cannuala inserted into the access site is blocked by the floor from damaging said pressure transmissive diaphragm.

20. The apparatus of claim 19 wherein the needle guard portion further comprises:

a wall and at least one window in the wall for allowing received fluid to flow into and out of the needle guard portion.

* * * * *